United States Patent [19]

Armstrong et al.

[11] Patent Number: 5,715,810
[45] Date of Patent: *Feb. 10, 1998

[54] INHALATION DEVICES

[75] Inventors: John C. Armstrong, Milton; Richard C. J. Palson, Medfield, both of Mass.

[73] Assignee: Sepracor Inc., Marlborough, Mass.

[ * ] Notice: The term of this patent shall not extend beyond the expiration date of Pat. No. 5,337,740.

[21] Appl. No.: 672,020

[22] Filed: Jun. 24, 1996

Related U.S. Application Data

[63] Continuation of Ser. No. 250,060, May 27, 1994, Pat. No. 5,529,059, which is a continuation of Ser. No. 735,924, Jul. 25, 1991, Pat. No. 5,152,722, which is a continuation of Ser. No. 738,924, Aug. 1, 1991, Pat. No. 5,337,740.

[51] Int. Cl.$^6$ ............................................. A61M 15/00
[52] U.S. Cl. .................................. 128/203.15; 128/203.21
[58] Field of Search ........................... 128/203.12, 203.15, 128/203.21

[56] References Cited

U.S. PATENT DOCUMENTS

| | | | |
|---|---|---|---|
| 2,519,555 | 8/1950 | Fields | 128/203.21 |
| 2,944,547 | 7/1960 | Ziherl et al. | 128/203.21 |
| 3,425,414 | 2/1969 | La Roche | 128/203.21 |
| 3,507,277 | 4/1970 | Altounyan | 128/203.21 |
| 3,635,214 | 1/1972 | Rand et al. | 128/203.15 |
| 3,659,598 | 5/1972 | Peters et al. | 128/204.24 |
| 3,888,252 | 6/1975 | Side et al. | 128/203.15 |
| 3,888,253 | 6/1975 | Watt et al. | 128/203.15 |
| 3,938,516 | 2/1976 | Mathes | 128/203.15 |
| 3,948,264 | 4/1976 | Wilke et al. | 128/203.15 |
| 4,014,336 | 3/1977 | Mathes | 128/203.15 |
| 4,064,878 | 12/1977 | Lundquist | 128/203.15 |
| 4,098,273 | 7/1978 | Glenn | 128/203.21 |
| 4,105,027 | 8/1978 | Lundquist | 128/203.21 |
| 4,240,418 | 12/1980 | Rosskamp et al. | 128/203.15 |
| 4,291,688 | 9/1981 | Kistler | 128/200.23 |
| 4,338,931 | 7/1982 | Cavazza | 128/203.15 |
| 4,627,432 | 12/1986 | Newell et al. | 128/203.15 |
| 4,778,054 | 10/1988 | Newell et al. | 128/203.21 |
| 4,811,731 | 3/1989 | Newell et al. | 128/203.15 |
| 4,995,385 | 2/1991 | Valentini et al. | 128/203.21 |
| 5,035,237 | 7/1991 | Newell et al. | 128/203.15 |
| 5,337,740 | 8/1994 | Armstrong et al. | 128/203.15 |
| 5,529,059 | 6/1996 | Armstrong et al. | 128/203.15 |

FOREIGN PATENT DOCUMENTS

| | | |
|---|---|---|
| 2020425 | 7/1990 | Canada . |
| 2 297 054 | 8/1976 | France . |
| 2 352 556 | 12/1977 | France . |
| 2 454 813 | 11/1980 | France . |
| 174811 | 8/1975 | New Zealand . |
| 179725 | 6/1978 | New Zealand . |
| 179724 | 7/1978 | New Zealand . |
| 2 129 691 | 5/1984 | United Kingdom . |
| 2 142 246 | 1/1985 | United Kingdom . |
| 2 169 265 | 7/1986 | United Kingdom . |
| 2 178 965 | 2/1987 | United Kingdom . |
| 0 467 172 | 7/1991 | United Kingdom . |

OTHER PUBLICATIONS

Product Literature, *Lyphodose*, of Falois.

*Primary Examiner*—Aaron J. Lewis
*Attorney, Agent, or Firm*—Pennie & Edmonds LLP

[57] ABSTRACT

The present invention provides devices for the oral or nasal inhalation of finely divided materials such as medicinal agents and drugs.

20 Claims, 7 Drawing Sheets

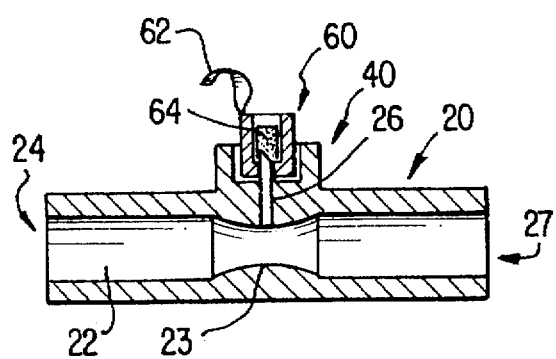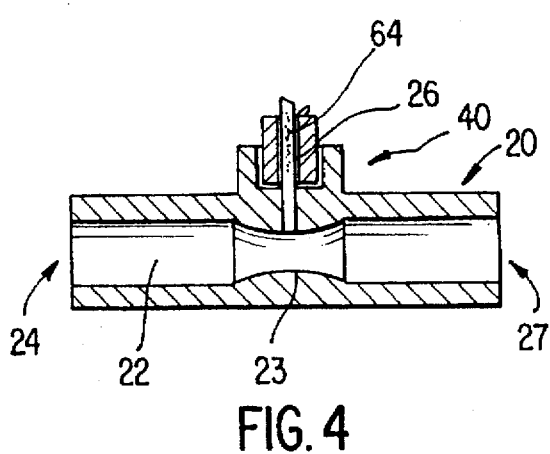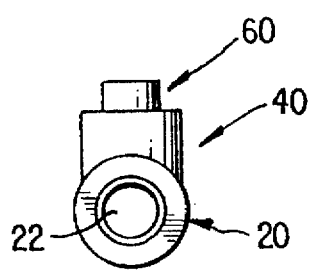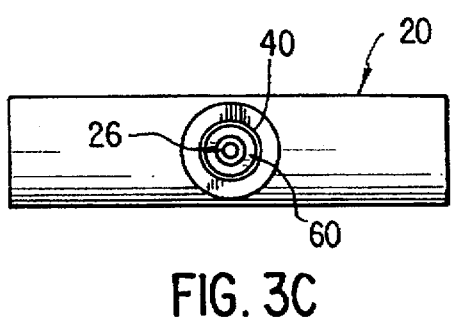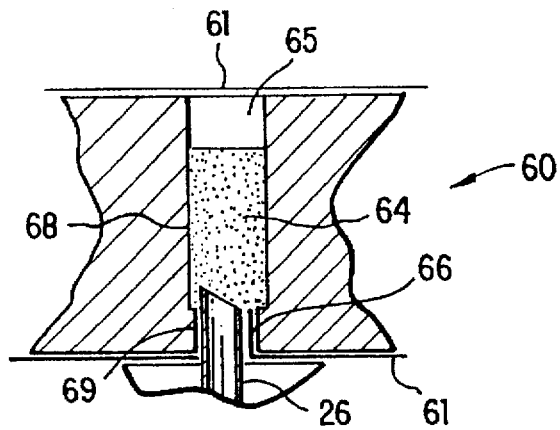

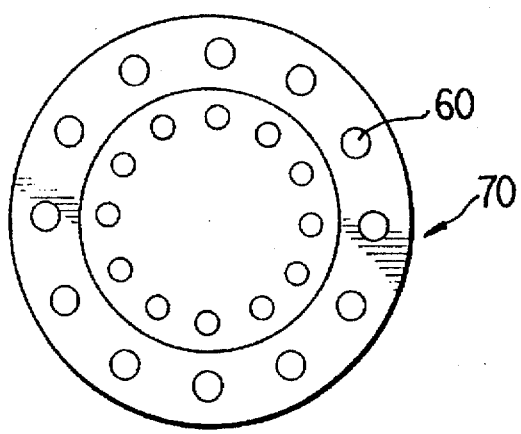
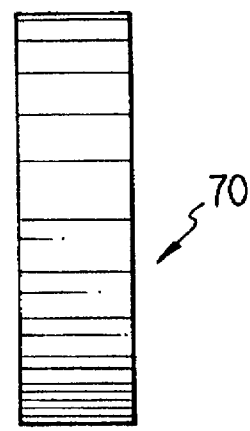
FIG. 7A  FIG. 7B
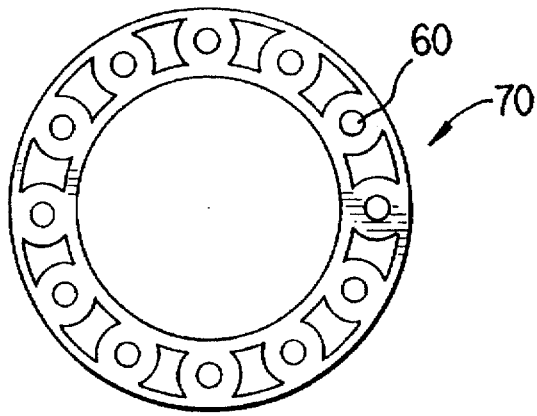
FIG. 7C
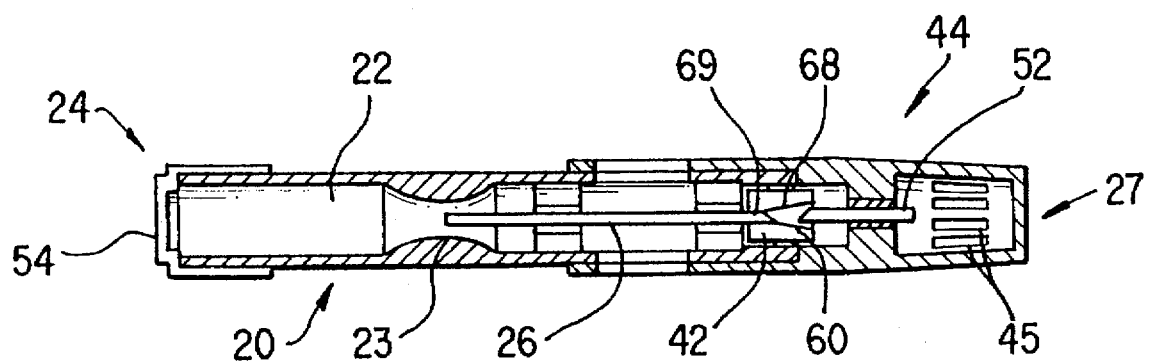
FIG. 8

INHALATION DEVICES

This is a continuation of U.S. patent application Ser. No. 08/250,060, filed May 27, 1994, now U.S. Pat. No. 5,529,059, which is CIP Ser. No. 738,924 filed Jul. 25, 1991 Pat. No. 5,152,722 which is a continuation of U.S. patent application Ser. No. 07/738,924, filed Aug. 1, 1991, now U.S. Pat. No. 5,337,740.

BACKGROUND OF THE INVENTION

This invention relates to devices for the oral or nasal inhalation of finely divided materials, such as medicinal agents and drugs.

Certain diseases of the respiratory tract are known to respond to treatment by the direct application of medicinal agents. As many such agents are most readily available as a finely divided material, e.g., in dry powdered form, their delivery is most conveniently accomplished by inhaling the finely divided material through the nose or mouth. This results in better utilization of the medicinal agent in that it is deposited exactly at the site desired and where its action may be required; hence, very minute doses of the therapeutic agent are often equally as efficacious as larger doses administered by other means, with a consequent marked reduction in the incidence of undesired side effects. Alternatively, the therapeutic agent in this form may be used for treatment of diseases other than those of the respiratory system. When the drug is deposited on the very large surface areas of the respiratory tract, it may be very rapidly absorbed into the blood stream; hence, this method of application may take the place of administration by injection, tablet, or other conventional means.

A variety of inhalation devices for the delivery of finely divided materials are known in the art. For example, U.S. Pat. No. 4,240,418 discloses inhalation devices wherein a container of finely divided material is positioned so that the material from the container can pass by gravity to a delivery area of the device from which it is dispensed. Accordingly, these devices suffer the disadvantage that the user must maintain the device in a particular position so that the finely divided material can pass by gravity to the collecting plate and it not dislodged therefrom prior to dispensing. It appears that such devices also require a large dispensing passage to prevent interference with the free fall of a relatively large load of the finely divided material.

Other known inhalation devices incorporate a deflector (U.S. Pat. No. 4,098,273) or a hollow tube (U.S. Pat. No. 3,938,516) to divert air flow into a chamber to dislodge the finely divided material, thereby requiring a substantially flow of air to disperse the finely divided material. Inhalation sufficient to create such a substantial flow of air is difficult for some users, e.g., asthmatics. Furthermore, it is believed that such devices deliver somewhat imprecise doses due to the inevitable variations in residue of finely divided material left behind in the container after dispensing.

Some known inhalation devices use members which vibrate to dispense the finely divided material, thus increasing the complexity and bulk of the device. For example, the devices of U.S. Pat. No. 3,948,264, utilize batteries to activate vibrators. Other devices incorporate breath activated vibratable members to disperse the finely divided materials. See, e.g., U.S. Pat. Nos. 3,888,253 and 4,995,385 which include a member which vibrates in the airflow to dispense the finely divided material. Still other known devices use a breath activated propeller device to spin the container of finely divided material, thereby casting the material out by centrifugal force, e.g., U.S. Pat. No. 3,507,277. A relatively high velocity of air flow is required to activate such devices, again a problem for breath impaired users.

Moisture in most powders tend to cause agglomeration and clumping thereby inhibiting the breakup and dispersion of the finely divided medication, an essential step in effective dispensing of the material. However, the manner in which many known devices operate renders hermetic sealing of the container of finely divided material impossible. In still other known devices, the containers for finely divided materials are gelatin capsules which are susceptible to atmospheric moisture.

In some known inhalation devices, e.g., conventional aerosol bronchodilators, drug delivery is achieved by the sometimes difficult coordination of digital force with voluntary inhalation.

New and more potent drugs which can be used in increasingly small quantities are being developed on an ongoing basis. In most instances, known inhalation devices for finely divided materials are not capable of delivering such small quantities without the addition of a significant amount of filler. It is highly desirable to minimize the use of such fillers, e.g., in order to reduce the likelihood of side effects.

It can be seen that presently known devices for the delivery of finely divided materials suffer disadvantages which include imprecise delivery, inability to deliver directly from a hermetically sealed container, high breath demands upon the user, limited portability due to bulk, and complexity of design. Thus, alternative inhalation devices are being sought.

SUMMARY OF THE INVENTION

Devices of the present invention utilize air flow through a container of finely divided material, the container having one section open to the atmosphere and another open to the interior of the device, to dispense the finely divided material. As air is drawn through the container and the device by oral or nasal inhalation of the user, increased air velocity causes decreased pressure within the device. This results in a pressure differential between the section of the container open to the atmosphere and the section open to the body member. The resultant flow of air from outside atmospheric pressure to inside partial vacuum picks up the finely divided material carrying it into the device to mix with the internal flow of air. The passage of air through the container of finely divided material, and the device virtually purges the material from both the container and the device, thereby carrying it along with the user's inspired breath to the lungs or nasal passages.

The inhalation devices of the present invention overcome many of the disadvantages associated with known devices. One important advantage resides in their ability to accurately and repeatedly dispense the finely divided material. Because it is air flow through the finely divided material that causes dispensing, the air flow through the container typically causes virtually all of the finely divided material to be evacuated. Another advantage of devices in accordance with the present invention is that loads of finely divided material as low as about 0.1 mg can be dispensed. This is also an important advantage because by dispensing small doses of finely divided materials, such as pharmaceuticals, the use of fillers, such as lactose, is minimized.

Yet another major advantage of inhalation devices in accordance with the present invention is the total protection of the finely divided material up to the moment of use. Each individual dose is hermetically sealed, in some cases removably hermetically sealed, to assure as long a shelf life as possible and freedom from contamination.

Furthermore, the present inhalation devices require little or no coordination on the part of the user, since inhalation of breath causes the device to function. In one embodiment, the user need only press down on a conveniently located button to perforate the container of finely divided material to ready the device for use. The finely divided material remains in the container until activated by patient inhalation which can occur within any reasonable time period after the container seal is broken. Moreover, a relatively low velocity of air flow through the body member, as measured by a standard flow meter, is adequate to achieve full dispensing, generally even for a child.

The inhalation devices of the present invention have the further advantage of great simplicity which renders them capable of being made in a small size for inconspicuous portability, further enhancing the desirability for use as a personal dispenser. One preferred inhalation device of the present invention is pen-like in design to render it easy to use inconspicuously, as well as to provide other important advantages.

The devices disclosed herein are adapted for receiving from a single to multiple containers of finely divided material. In one preferred embodiment, the device is adapted to receive a circular disk containing multiple containers of finely divided material. Not only does this embodiment provide a convenience for the user, it also provides an economy in production filling.

One inhalation device in accordance with the present invention comprises (i) a body member having an air passageway therethrough, one end of the body member being adapted for insertion into the mouth or nose of the user; (ii) a holder connected to the body member for receiving at least one removably sealed container of finely divided material; and (iii) at least one piercer for piercing the removably sealed container while the sealed container is in the holder, the piercer extending from the body member and into the holder and having a passageway therethrough open to the body member and the holder. A removably sealed container is placed in the holder thereby causing the piercer to pierce the sealed container. The removable seal is then removed and air drawn through the unsealed and pierced container, the piercer, and the body member cooperate to cause finely divided material disposed in the container to be dispensed therefrom.

In another similar embodiment of the present invention, the piercer extends from the body member through the holder for a distance greater than the dimension of the sealed container to be pierced, thus, providing devices for the oral or nasal inhalation of finely divided materials from a sealed container which need not be provided with a removable seal. In such embodiments, the dimensions of the piercer are such that when the sealed container is placed in the holder thereby causing the piercer to pierce through the sealed container therein, the finely divided material is transferred from the container to the air passageway of the piercer as it passes through the container. Subsequently, air drawn through the piercer and the air passageway of the body member cooperate to cause the finely divided material disposed in the piercer to be dispensed therefrom.

The present invention provides yet another inhalation device for dispensing finely divided materials from a sealed container which is not provided with a removable seal. Such devices typically include at least two piercers and comprise:

(i) a body member having an air passage therethrough, one end of the body member being adapted for insertion into the mouth or nose of the user; (ii) a holder for receiving at least one sealed container of finely divided material, the holder being connected to the body member; (iii) at least one first piercer for piercing the sealed container while in the holder, the first piercer extending into the interior of the holder and having an air passageway therethrough open to the body member and the holder; (iv) at least one second piercer for piercing the sealed container while in the holder the second piercer extending into the holder and having a air passageway therethrough, open to the interior and exterior of the holder; and (v) engaging means for causing the first and second piercer, while the sealed container is in the holder, to pierce the sealed container.

These devices operate so that when the sealed container is positioned in the holder and the engaging means causes the first and second piercers to pierce the sealed container to create an air passageway therethrough, air drawn through the first piercer, the pierced container, the second piercer, and the passageway of the body member cooperate to cause finely divided material disposed in the pierced container to be dispensed therefrom.

BRIEF DESCRIPTION OF THE DRAWINGS

In the drawings:

FIG. 3A is a section on line 3A—3A of the device shown in FIG. 1, showing a cross-section of a container of finely divided material disposed therein, wherein the removable seal has been removed.

FIG. 3B is an end view of the device shown in FIG. 1.

FIG. 3C is a plan view of the device shown in FIG. 1.

FIG. 4 is a cross-sectional view of yet another embodiment of a device of the present invention, similar to that shown in FIG. 3.

FIG. 5 is an enlarged cross-sectional view of the removably sealed container of finely divided material shown in FIG. 3A wherein the removable seal is intact.

FIG. 7A is a plan view of a disk provided with multiple sealed containers containing finely divided materials for use in the present invention.

FIG. 7B is a side view of the disk shown in FIG. 7A.

FIG. 7C is a bottom view of the disk shown in FIG. 7A.

FIG. 8 is a cross-sectional view of another device in accordance with the present invention, showing a cross-sectional view of a tapered container.

DETAILED DESCRIPTION OF THE INVENTION

Although the inhalation devices of the present invention are primarily illustrated by means of devices which have been adapted for oral inhalation, it will be appreciated by those skilled in the art that such devices may also be adapted for nasal inhalation of finely divided materials.

Figure 1:
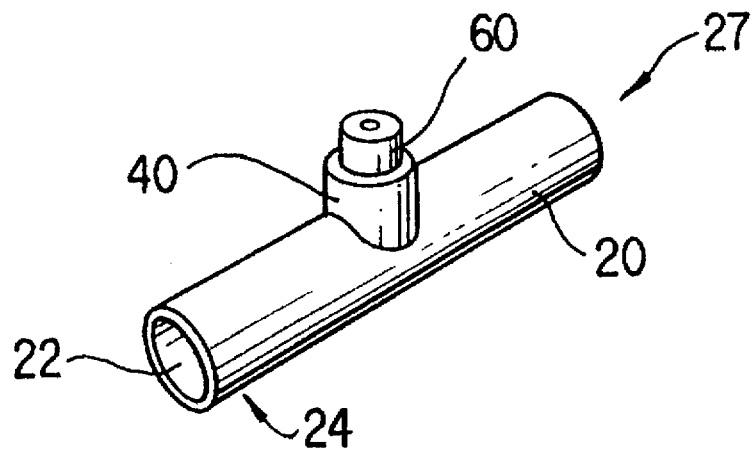
FIG. 1 is an perspective view of one embodiment of a device in accordance with the present invention.

Referring now to FIGS. 1 and 3 there is shown one embodiment of an inhalation device of the present invention for the oral inhibition of finely divided materials from a removably sealed container. The device shown comprises a body member 20 having an air passageway 22 therethrough, the air passageway comprising a venturi. One end 24 of the body member 20 is adapted for insertion into the mouth of the user. The other end 27 is an air intake end and may optionally be provided with a screen (not shown) to filter inhaled air. A holder 40, comprising an open receptacle for receiving at least one removably sealed container 60 of finely divided material 64, is connected to body member 20. At least one piercer 26 (shown in FIG. 3A) for piercing the removably sealed container 60, while the sealed container 60 is in the holder 40, extends from the body member 20 and into the holder 40. The piercer 26 has a passageway therethrough open to the body member 20 and the holder 40.

The container 60 is dimensioned to extend above the holder 40 while present therein so that the user can access the removable seal 62 and can grasp and remove the container 60 after use. An enlarged cross-sectional view of a removably sealed container is shown in FIG. 5. In use, the removably sealed container 60 is placed in the holder 40 thereby causing the piercer 26 to pierce the sealed container 60 and to hold the tab of sealing material 66 created thereby (See, e.g., FIG. 5) against the container 40. The removable container seal 62 is then removed, thereby creating an opening to the atmosphere.

The device shown in FIG. 4 is similar to that shown in FIG. 3. However, it is adapted for use in conjunction with a sealed container which is not provided with a removable seal. The piercer 26 in this device extends from the body member 20 through the holder 40 for a distance greater than the dimension of the sealed container 60 to be pierced. When the sealed container 60, is placed in the holder 40 as shown in FIG. 4, thereby causing the piercer 26 to pierce through the sealed container 60, the finely divided material 64 is transferred from the container 60 to the air passageway of the piercer 26 from which it is dispensed upon inhalation by the user.

In use, the mouthpiece 24 of the inhalation devices of the present invention is placed inside the lips of the user to minimize impingement of the finely divided material on the mouth. A quick intake of breath causes air to flow through the air intake end 27 and into air passageway 22 of body member 20 to create a partial vacuum, thereby causing the finely divided material 64 to be dispensed from (i) the pierced and unsealed container 60 in the embodiment shown in FIGS. 1, 3, and 9; and (ii) from the air passageway of the piercer 26 in the embodiment shown in FIG. 4.

Figure 2:
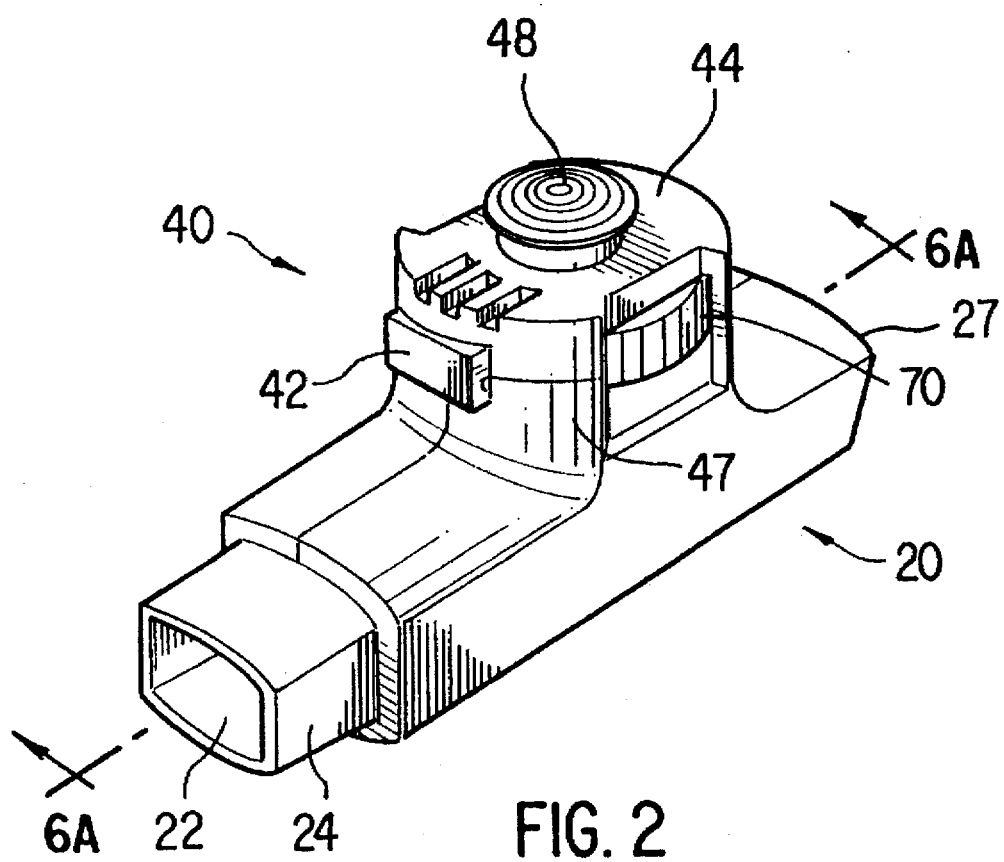
FIG. 2 is an perspective view of another embodiment of a device according to the present invention.
Figure 6A:
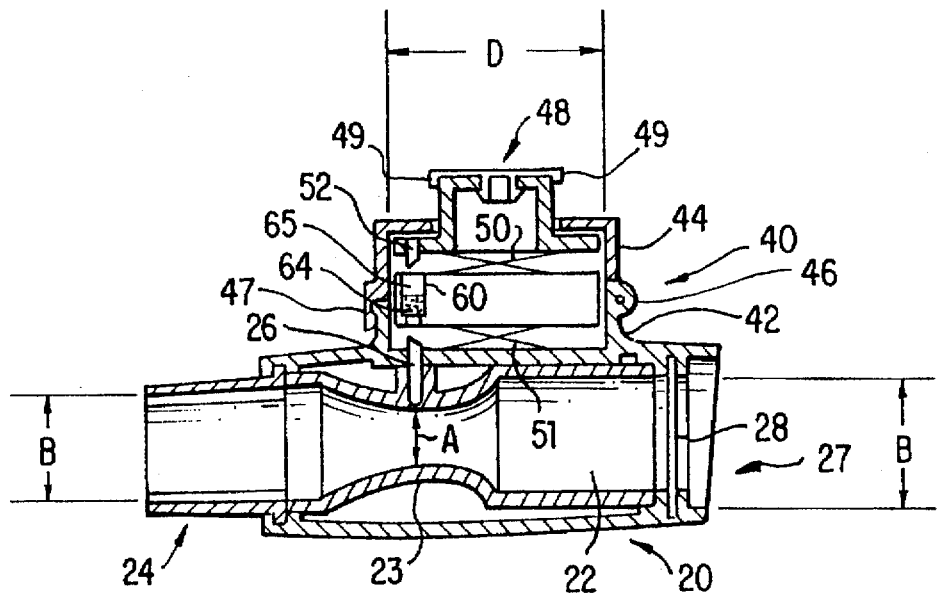
FIG. 6A is a cross-sectional view of the device shown in FIG. 2 taken along line 6A—6A of FIG. 2A.
Figure 6B:
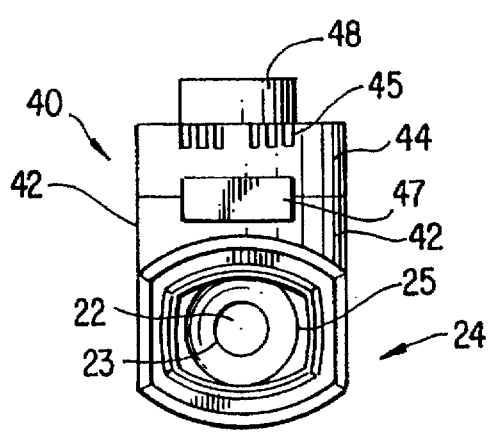
FIG. 6B is an end view of the device shown in FIG. 2 showing the inhalation end.
Figure 6C:
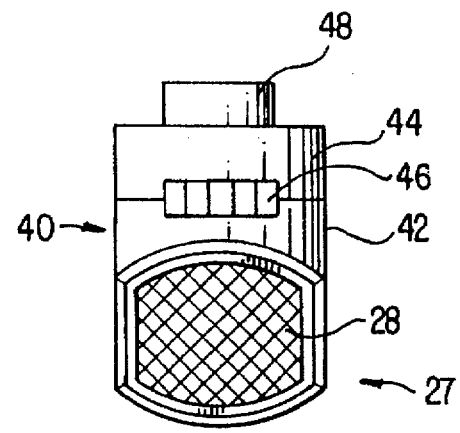
FIG. 6C is an end view of the device shown in FIG. 2 showing the air intake end.
Figure 6D:
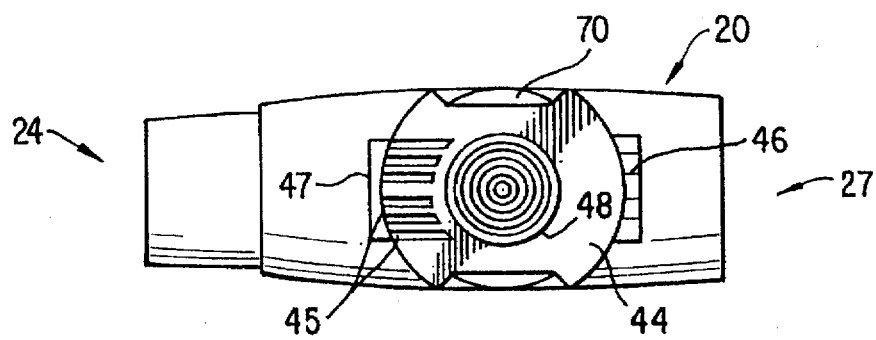
FIG. 6D is a plan view of the device shown in FIG. 2.
Figure 9A:
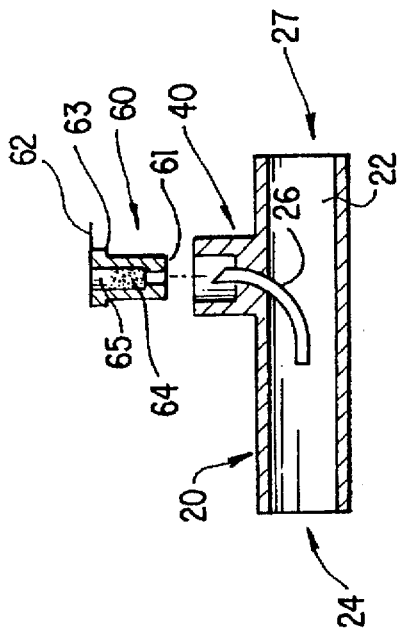
FIGS. 9A–9D are cross-sectional view of yet other devices in accordance with the present invention.
Figure 9B:
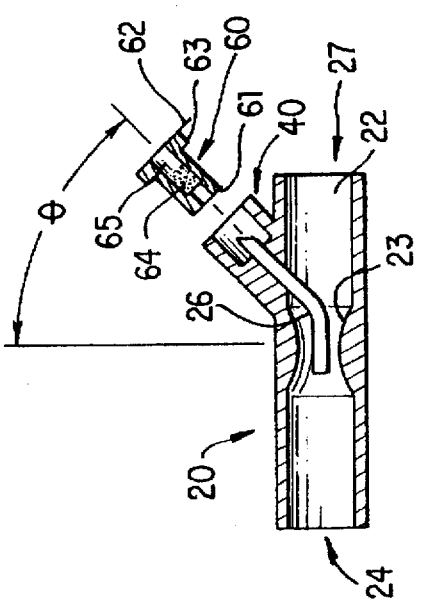
Figure 9C:
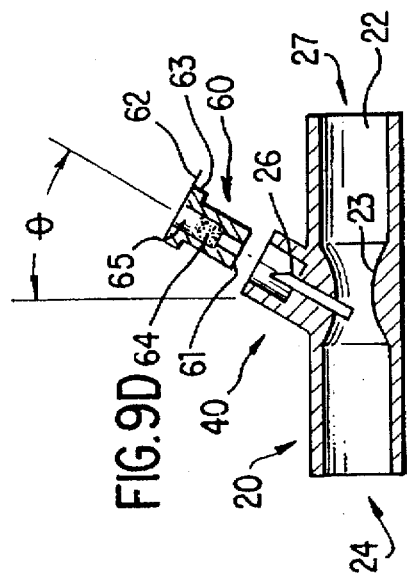
Figure 9D:
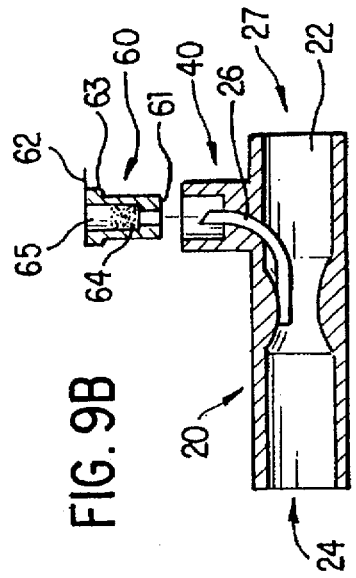

Another preferred device in accordance with the present invention, shown in FIGS. 2 and 6, comprises a body member 20 having an air passageway 22 therethrough, and a holder 40. One end 24 of the body member 20 is adapted for insertion into the mouth of the user. The other end 26, the air intake end, of body member 20 is provided with a screen 28 to minimize inhalation of undesired materials, e.g., dust, which may be present in the air. A first piercer 26 for piercing the sealed container 60 while in the holder 40, extends into the interior of the holder 40 and has a passageway therethrough open to the body member 20 and the holder 40.

In the embodiment shown in FIGS. 2 and 6, the holder 40 is adapted to receive a disk 70 provided with multiple containers 60 as shown in FIG. 7. The holder 40 comprises a receptacle 42 fixed to the body member 20 and a cover 44 movably attached to receptacle 42 by hinge means 46. The disk 70 while in the holder 40 is rotably, centrally disposed on a pin (not shown) which is mounted therein.

The disk 70 is provided with a conventional locking means so that during rotation, the disk is located in position each time a container of finely divided material is disposed adjacent piercers 26, 52, thereby locating each single dose container 60 for dispensation. Disks of a given diameter can contain different numbers of single doses depending upon the requirements of the particular drug in use. Thus, one inhalation device in accordance with the present invention can have many different drug applications.

A preferred multiple cavity disk 70 is about 0.75 to 1.25 inches in diameter, about 0.250 to 0.312 inches deep and is provided with individual sealed containers, similar to those shown in FIG. 5. The disk 70 is typically made of conventional molded plastics, such as, polypropylene, polyethylene, acetal, ABS and so forth. However, other conventional materials known to those skilled in the art may also be used. Although disk 70 can be rotated mechanically after use, for simplicity the preferred method is hand rotation. It will be apparent to those skilled in the art that the disk 70 could be replaced with multiple container strips, either rigid or in flexible rolls, e.g., as in a cartridge belt for an automatic weapon, and so forth.

The cover 44 is provided with perforations 45 to provide an opening to the atmosphere through which air is drawn upon inhalation by the user when the pierced container 60 is in the device. The cover is also provided with a section 48 having a first leaf spring 50. Section 48 is movably mounted in the cover 44, flanges 49 providing stops to maintain section 48 in cover 44, when cover 44 is raised to insert a disk 70 of sealed containers 60.

A second piercer 52 mounted in cover section 48 extends into the interior of the holder 40 and has a passageway therethrough open at both ends to the holder 40. The second piercer 52 is positioned relative to the first piercer 26 so that they are capable of cooperating to pierce the sealed container 60 when the sealed container 60 is in receptacle 42 and rotated into dispersing position adjacent piercers 26, 50.

Receptacle 42 is provided with a second leaf spring 51 disposed between body member 20 and disk 70, when the disk 70 is in holder 40. The movable cover section 48 cooperates with leaf springs 50, 51 to provide the engaging means for causing the first and second piercers 26, 52 to pierce the sealed container 60 while in the holder 40 when movable cover section 48 is pressed towards container 60 by the user.

To operate the device shown in FIGS. 2 and 6, the movable cover section 48 is depressed by the user so that piercers 26 and 52 pierce the seals 61 (shown in FIG. 5) of the container 60 of finely divided material 64, thereby creating an air passage. The air passage is blocked only by the finely divided material 64, because the tab of pierced seal 66 is held against the side of holder 40 by piercer 26 (see FIG. 5). The movable cover section 48 is held in a depressed position until after inhalation by the user so that the piercers 52, 26 will remain in contact with the container 60 of finely divided material 64. The passage of air through the perforation in seal 62, needle 52, container 60, needle 26, and air passageway 22, virtually purges the finely divided material 64 from the container 60, carrying it along with the patients inspired breath into the lungs.

In preferred embodiments of the present invention, the air passageway 22 of the body member 20 comprises a venturi or a tube, wherein the first piercer 26 is disposed at or adjacent the smallest diameter of the venturi or the midpoint of the tube. A venturi is a particularly preferred configuration for the air passageway 22 of the body member as shown, e.g., in FIGS. 3A, 4, 6A and 8.

In one particularly preferred embodiment of the present invention, the body member 20 has a major diameter at each end ("B" in FIG. 6A) of about 0.3 to 0.8 inches with, in the case of embodiments wherein the air passageway 22 composes a venturi, a minor diameter ("A" in FIG. 6A) at the venturi's point of restriction 23 of about 0.2 to 0.5 inches. These dimensions are based upon end 24 of body member 20 being adapted for insertion into the nose or mouth of the user, as well as providing a minor diameter adequately large to allow an uninhibited intake of breath. The inner diameter ("D" in FIG. 6A) of holder 40 is dimensioned to receive disk 70 and may be from about 0.5 to 1.5 inches when A and B have the dimensions set forth above. It is understood that the circumstances of use will dictate the dimensions without altering the intent of the device. For example, one might wish the unit to resemble a pocketable pen as shown in FIG. 8 to achieve an enhanced degree of portability.

The relative dimensions of the containers of finely divided material for use in the devices of the present invention and the piercer(s) of such devices are selected to provide accurate delivery of the finely divided material. The dimensions of the piercer 26 which opens to body member 20, as well as the end or ends of the container 60 pierced thereby, are selected to minimize entrapment of the finely divided material 64 adjacent piercer 26. Finely divided material below the orifice of the needle 26 is unlikely to evacuate, yet the needle 26 must project high enough to hold tab 66 (shown in FIG. 5) in a vertical position. If tab 66 is not held parallel to the sides of the container, it may be drawn down by the vacuum created upon inhalation to seal off piercer 26, thereby upsetting dosage accuracy.

In some preferred embodiments of the present invention, the diameter of the cylindrical container is stepped down at the end disposed adjacent piercer 26 while in the device, to minimize entrapment of the finely divided material. See, e.g., stepped down section 69 in FIG. 5. The step is preferably equal in length to the outside diameter of piercer 26 (i.e., about the size of tab 66 in the vertical position). The diameters of piercer 52 are not as important since the tab created by piercer 52 is not positioned so that it will interfere with dispensing of the finely divided material. However, piercer 52 must be sufficiently large to permit unobstructed flow of air.

The inhalation devices of the present invention shown in the figures embody a piercer 26 which comprises a needle, preferably sharpened at the piercing end to about a 30° to 45° angle. The rim of the needle opposite the apex of the needle point is typically blunted to avoid cutting a piece of the seal 61 of container 60 free. As shown in FIG. 5, this leaves a tab 66 of the seal "hinged" to the container 60 thereby preventing ingestion.

In a preferred embodiment the needle 26 has an inner diameter of about 0.01 to 0.15 inches and an outer diameter of about 0.03 to 0.170 inches. Such inside diameters afford adequate flow of finely divided material while still retaining it in the container 40 until the moment of discharge. However, diameters outside the preferred ranges may be useful, depending in part upon the fluidity of the finely divided material. For example, a highly fluid finely divided material would call for a smaller diameter needle 26 than less fluid material in order to hold the powder inside the container 40 until evacuated by the inhalation of the user.

In preferred embodiments of the present invention, other than those similar to the embodiment shown in FIG. 4, the needle 26 extends into the container 60 for approximately one needle diameter length, plus the length of the sharpened angle, or sufficiently far to hold tab 66 in a position generally parallel to the side of the needle 26 and adjacent the inner wall of the container 40, thereby leaving a clear passage for air flow. This enables tab 66 to remain attached to the container 40 and to be bent to a position as shown in FIG. 5.

In embodiments wherein the needle 26 preferably has an inner diameter of about 0.01 to 0.15 inches and an outer diameter of about 0.03 to 0.170 inches, section 69 of the container has an inner diameter of about 0.035 to 0.180 inches, and section 68 has a diameter of about 0.045 to about 0.190 inches. In a particularly preferred embodiments piercer 26 has an inner diameter of about 0.045 inches and an outer diameter of about 0.062 inches and the section 68 of container 60 has an inner diameter of about 0.070 inches and section 69 has an inner diameter of about 0.080 inches.

In embodiments of the present invention which include a second piercer 52, such as those shown in FIGS. 2, 6 and 8, the second piercer 52 is also preferably sharpened at the piercing end to about a 30° to 45° angle and the rim opposite the apex of the point is typically blunted. The inner diameter of piercer 52 is typically about 10 to 15% greater than the inner diameter of piercer 26.

In the embodiment shown in FIGS. 2 and 6, leaf springs 50 and 51 are preferably stainless steel and are about 0.005 to 0.015 inches, more preferably about 0.010 to 0.012 inches. Molded plastic springs can also be used but the extra thickness of such springs may be undesirable.

The configuration and dimensions of containers for use in the inhalation devices of the present invention are adapted to the particular device. For example, in embodiments wherein the piercer 26 is a needle, the container is preferably cylindrical. In some embodiments, the diameter of the container 60 is constant throughout, e.g., as shown in FIG. 4. In other embodiments, the container is provided with a first section 68 and a second section 69, narrower in diameter than section 68, as shown in, e.g., FIG. 5. In yet other embodiments of the present invention, e.g., as shown in FIG. 8, section 68 of container 60 tapers outwardly. This taper allows a greater volume of finely divided material to be loaded within a given depth. For proper evacuation of the container 60, the taper should not exceed an angle of about 10° to 15°.

In the embodiments shown in the figures, other than embodiments similar to the embodiment shown in FIG. 4, the inner diameter of section 68 of the container 60 is about 10 to 15% larger than the outer diameter of needle 26. In embodiments similar to that shown in FIG. 4, because the finely divided material is transferred to the needle as it pierces the container, the inner diameter of the container is only about 10 to 15% larger than the outer diameter of needle 26 to minimize any residue of finely divided material which may be left behind in the container.

The amount and fluidity of the finely divided material to be delivered will in large part determine the dimensions of the inhalation devices of the present invention. The devices of the present invention are capable of delivering amounts of finely divided material ranging from about 0.1 to 25 milligrams.

The dimensions of containers of the finely divided material for use in the present invention are also adapted for the particle size and amount of such material to be dispensed and, preferably, are large enough to provide an empty space 65 above the surface of the finely divided material. See, e.g., FIG. 5. This space 65 allows the finely divided material 64 to remain loose, avoiding agglomeration in storage and compaction from pressure as the needle 26 penetrates the container 60. In preferred embodiments, the container 60 is about half filled with finely divided material 64.

The particle size of the finely divided material to be delivered also influences the dimensions of the devices of the present invention. The desired particle size is determined, in part, by the mode of delivery, i.e., orally or nasally. Generally in oral administration, the intent is to get the greatest possible portion of the dose of finely divided material into the lungs and to avoid impingement on the lining of the buccal cavity. Whereas for nasal administration, it is desirable to have the major portion of the powder dose deposited on the nasal mucosa and the minimum amount carried to the lungs. A finer particle size and greater flow of air through the device of the present invention is used in oral delivery as compared with nasal delivery to accomplish the desired end. It is believed that the minimum air flow that would discharge the powder fully would also minimize the amount of powder carried to the lungs for nasal applications.

Containers for use in the present invention are sealed at one or both ends with a conventional piercable material, such as a plastic or metal film, using methods known to those skilled in the art. See, e.g., film 61 in FIG. 5. In such embodiments, the thickness of the film is about 0.002 to 0.004 inches. The desired characteristics for such sealing materials are high tensile strength to avoid tearing during perforation and resistance to the passage of moisture. In a preferred embodiment, a polyester film having heat activating adhesive on one side is used to seal the containers. Although polyester is preferred, other films known in the art, such as aluminum foil, may also be employed. In one preferred embodiment of the present invention wherein the container is removably sealed, the removable seal comprises a hermetic foil seal which is provided with an integral tab for ease of manual removal.

In the manufacture of embodiments of the present invention wherein multiple enhancers 60 are disposed in disk 70, the disk 70 is typically first sealed on one side with a piercable sealing material. The finely divided material 64 to be dispensed is then added to the multiple containers 60 disposed in disk 70 and the containers 60 are then hermetically sealed by sealing the other side of the disk 70 either with a removable seal or with piercable sealing material.

The devices and containers of the present invention are made from conventional materials and by conventional techniques known to those of ordinary skill in the art. To ensure simple manufacture of such devices and containers, it is advantageous to use a readily processable plastic where suitable.

It will be apparent to the skilled artisan in light of the teachings of the present invention that configurations of body member 20, holder 40, piercer 26 and/or and piercers 26, 52 other than those shown may be utilized without departing from the spirit and scope of the invention.

For example, holder 40 may be connected to the body member 20 at various angles as illustrated in FIG. 9: FIG. 9A showing a 45° angle, FIGS. 9B and 9C a 90° angle, and FIG. 9D a 30° angle. In yet another embodiment shown in FIG. 8, body member 20, holder 40, and piercers 26 and 52 are arranged in parallel, i.e., at 0° angle. Furthermore, the embodiment shown in FIG. 8 in pocketable and less conspicuous in use, being somewhat pen-like in appearance.

In use, the cover 44 of the embodiment shown in FIG. 8 is removed, the sealed container 60 is inserted in the holder 40, and the bottom seal of container 60 is pierced. The cover 44 is replaced and pressed home to pierce the top seal. After removing the dust cap 54, the user places the mouthpiece 24 in the mouth and inhales. In preferred embodiments, the dimensions are as follows: overall length, about 3 to 6 inches; diameter, abut 0.25 to 0.75 inches; length of body member 20, about 2 to 4 inches; length of cover 44, about 1.5 to 2.5 inches; length of piercer 26, about 1 to 1.75 inches; and length of piercer 52, about 0.375 to 0.75 inches. In one such preferred embodiment for oral inhalation the breath required for actuation of the device was only about 25 liters per minute. The dimensions of this device were as follows: overall length of about 3.375 inches; an inside diameter of about 0.32 inches at the widest section and 0.25 inches at the narrowest section of the venturi; body member 20 length of about 2.25 inches; holder 40 length of about 0.375 inches; piercer 26 length of about 1.1 inches; and piercer 52 length of about 0.5 inches.

In the adaptations of the embodiment shown in FIG. 8 for nasal inhalation, the internal diameter is reduced to restrict the air flow for delivery. For example, the narrowest section of the venturi can be reduced to about 0.187 inches in diameter to restrict the air flow. Furthermore, end 24 of the body member 20 is adapted to fit the human nose, and in some such embodiments, is bent upward at a 30° angle for comfort in use. Other than diameter, the basic dimensions are similar to those given above.

As is amply illustrated by the various embodiments in accordance with the present invention described herein, by following the teachings of the present invention one of ordinary skill in the art can vary the disclosed devices in structure by utilizing ordinary skill in the art to meet the demands of a particular finely divided material, particular user and so forth.

In order to illustrate the delivery advantages of the inhalation devices of the present invention, administration of cortisol tritiated ($H^3$-cortisol) using an inhalation device similar to that shown in FIGS. 1 and 3A are compared with conventional oral administration of $H^3$-cortisol by testing the urine of recipients of the $H^3$-cortisol for its presence.

Free, unmetabolized $H^3$-cortisol present in the urine reflects the amount of $H^3$-cortisol in circulation. By free cortisol is meant cortisol which has not been altered by the liver. It is known that when cortisol is ingested, a good portion is inactivated or metabolized in the liver.

Figure 10:
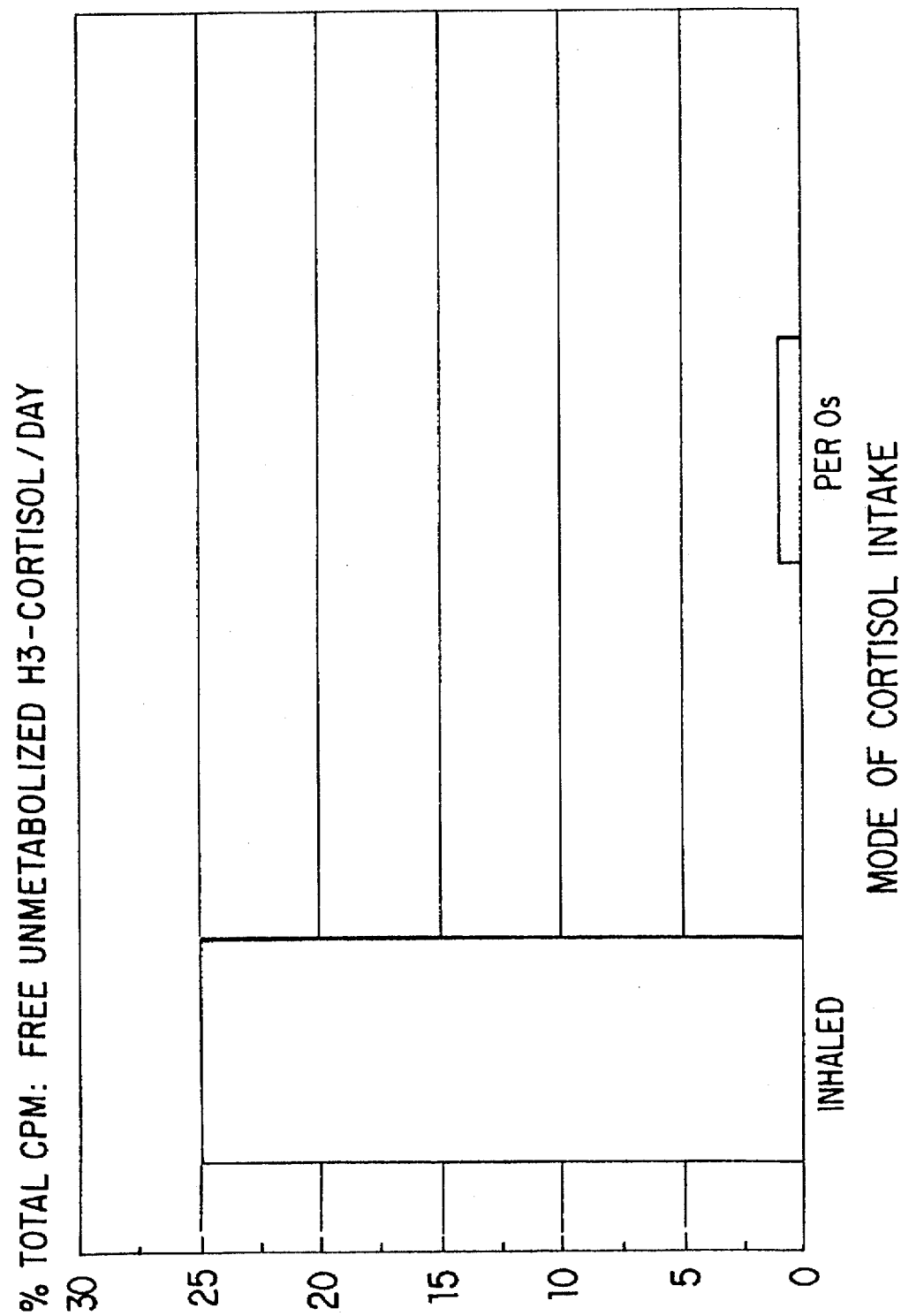
FIG. 10 is a graph showing total excretion of free $H^3$-cortisol for a 24 hour period after administration nasally in accordance with the present invention as compared with excretion of free $H^3$ cortisol after conventional oral administration.
Figure 11:
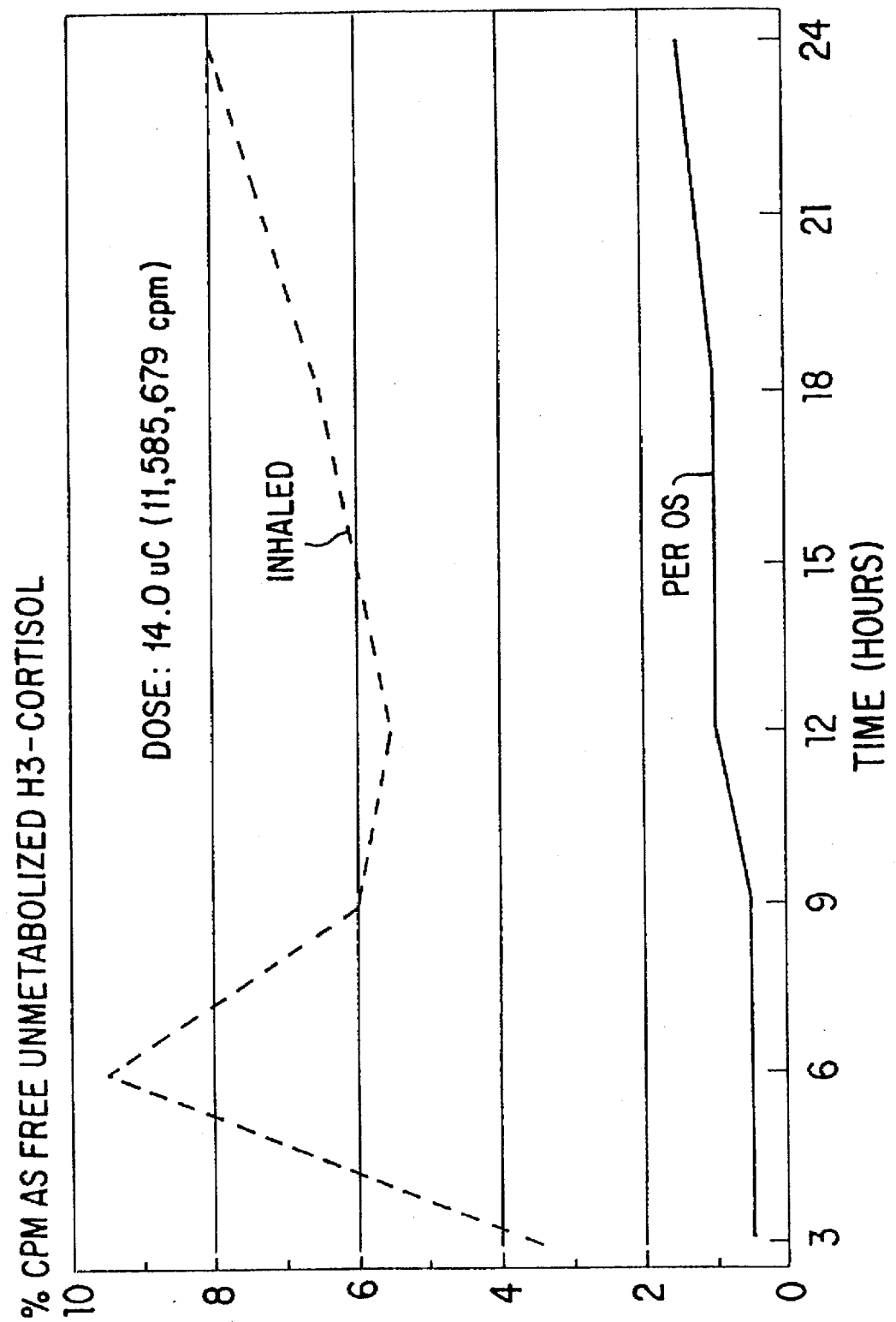
FIG. 11 is a graph showing excretion of free $H^3$-cortisol over a 24 hour period after administration nasally in accordance with the present invention as compared with excretion of free $H^3$ cortisol after conventional oral administration.

FIG. 10 shows that more free $H^3$-cortisol was excreted in a 24 hour period in the urine when the $H^3$ cortisol was administered via an inhalation device of the present invention as compared with ingestion. FIG. 11 shows that inhaled cortisol is more directly available for excretion in the urine at an earlier time than is ingested cortisol. These results give very powerful indirect evidence that the inhaled cortisol was not just swallowed but reached the alveolar epithelium and, thus, entered systemic circulation in a manner almost equivalent to delivery of $H^3$-cortisol intravenously. In contrast, the ingested cortisol was metabolized rapidly by the liver, because it was absorbed by the gut into the portal circulation.

A device similar to that shown in FIGS. 1 and 3A was tested to determine its delivery accuracy.

A container similar to that shown in FIGS. 3A and 5 was filled with about 3.24 mg of finely divided material and placed in the holder 40 of a device similar to that shown in FIGS. 1 and 3A. It was not necessary to provide the container with a removeable seal 62 because the finely divided material was dispensed immediately after being placed in the container. The method of discharge was by hand vacuum pump with a volume approximately equal to the human lung. A constant stroke was used in dispensing to minimize variation. Immediately after dispensing, the container was removed from the device and weighed again, and the residue of finely divided material determined. This process was repeated thirty-five times. The container was virtually purged with each delivery, and the residue remaining was very constant and very small. Thus, very accurate dose delivery was achieved by use of a device of the present invention.

This invention will be further understood with reference to the following examples which are purely exemplary in nature and are not meant to limit the scope of the invention.

EXAMPLE

Example 1

Administration of Tritiated Cortisol

A device similar to that shown in FIGS. 1 and 3A was used in this Example.

$H^3$-cortisol for inhalation and for oral ingestion was prepared as follows: 100 mg of cortisol was weighed in a clean crucible. 200 mμ of $H^3$-cortisol dissolved in ethanol was added to the powder, and thereafter, the ethanol was evaporated in a desiccator and the sample mixed well. The mixture of unlabelled and $H^3$-cortisol was ground with a stainless steel spoon shaped spatula. 5 mg of this mixture was weighed on glassene paper and then placed in a vial containing 0.5 ml of water and 5.0 ml of pico-fluor. Approximately 6,523,223 counts per minute/5 mg was prepared, giving a specific activity for $H^3$-cortisol of 1,279,063 counts/minute/mg.

10 mg of the $H^3$-cortisol was administered to one subject by use of an inhalation device of the present invention and to another subject orally.

The paper and tools used for weighing, as well as the inhalation device were washed with ethanol and the amounts of $H^3$-cortisol found were then appropriately subtracted from the counts obtained from dose inhaled and ingested.

Excretion of free, unmetabolized cortisol as tritium was counted after extraction from the urine into dichloromethane, which was dried down and counted. The measurement of free $H^3$-cortisol was carried out via conventional radioimmunoassay procedures after preliminary purification by thin layer chromatography.

FIG. 10 demonstrates that of the total counts per minute excreted, for a 24 hour period the percent as free $H^3$-cortisol was approximately 25% for the inhaled dose and less than 5% for the ingested dose.

FIG. 11 shows counts per minute of free $H^3$-cortisol excreted over a 24 hour period for both oral ingestion and inhalation of the same dose. It can be seen that there was an early rise in counts per minute of the free $H^3$-cortisol after inhalation which is not observed in the urine of an individual after oral ingestion of the labeled cortisol.

These results indicate that the inhaled $H^3$-cortisol reacted the alveolar epithelium and the systematic circulation, whereas the ingested cortisol was metabolized rapidly because it was absorbed by the gut into the portal circulation.

It is understood that the examples and embodiments described herein are for illustrative purposes only and that various modifications or changes in light thereof that will be suggested to persons skilled in the art are to be included in the spirit and purview of this application and the scope of the approved claims.

What is claimed is:

1. A device for oral or nasal inhalation comprising:

a body member having a first passageway therethrough, a first end of said first passageway for insertion into a mouth or nose of a user and a second end of said first passageway for intake of air responsive to a user's inhalation;

a holder connected to the body member between the first and seconds of the first passageway for receiving a container in an opening defined therein with a second passageway defined through the holder a first end of said second passageway communicating with the first passageway and a second end of said second passageway extending to an exterior of the body member for intake of air responsive to a user's inhalation; and at least one piercer positioned in the second passageway, wherein, air drawn through the first and second passageways is mixed before exiting the first end of the first passageway.

2. A device for the oral or nasal inhalation of a finely divided material comprising:

a body member having a first and second end with a first passageway extending therethrough and a second passageway associated with the first passageway between the first and second ends of the body member, said first passageway having an opening at the first end of the body member for insertion into a mouth or nose of a user and an opening at the second end of the body member for intake of air responsive to a user's inhalation, said second passageway communicating with the first passageway at a first end of the second passageway;

at least one container of finely divided material associated with the body member and communicating with a second end of the second passageway, said container defining a first and second sealed end in communication with the second passageway, each end of said container being unsealable to allow air to flow through the container and second passageway to expel the finely divided material from the first end of the second passageway; and at least one piercer positioned within the second passageway for unsealing at least one end of the at least one container, wherein when both ends of the container are unsealed, air drawn through the first passageway cooperates with air drawn through the container and second passageway to dispense the finely divided material from the container.

3. A device for oral or nasal inhalation comprising:

a body member having a sidewall and a first passageway therethrough, a first end of said first passageway for insertion into a mouth or nose of a user and a second end of said first passageway for intake of air responsive to a user's inhalation;

a holder connected to the sidewall of the body member between the first and second ends of the first passageways for receiving a container; and a least one piercer defining a second passageway therethrough, a first end of said second air passageway communicating with the first passageway and a second end of the second passageway communicating with the holder, wherein air drawn through the first passageway is mixed with air drawn through the second passageway upon a user's inhalation.

4. A device for oral or nasal inhalation which comprises:

a body member defining a sidewall and having a first passageway therethrough with a first end of the first passageway being adapted for insertion into a mouth or nose of a user, and a second end for intake of air responsive to a user's inhalation;

a holder connected to the body member for receiving a container; and at least one piercer extending from the first passageway, through the sidewall, and into the holder defining a second passageway therein open between the first passageway and the holder;

wherein air drawn through the first and second passageways is mixed before exiting the first end of the first passageway.

5. A device in accordance with claim 4, wherein the at least one piercer comprises a needle.

6. The device of claim 4, wherein the at least one piercer is approximately cylindrical and is configured and positioned to pierce a container received in the holder.

7. The device in accordance with claim 4, wherein the first passageway of the body member comprises a venturi disposed between the first and second ends of the first passageway, said venturi defining a minor diameter.

8. The device in accordance with claim 7, wherein the at least one piercer is positioned at the minor diameter.

9. The device in accordance with claim 4, wherein the piercer comprises a needle having a piercing end which is angled at about a 30° to 45° angle, said piercing end having an apex and a rim, said rim being located opposite said apex, with said piercing end being sharpened in the vicinity of the apex and blunted in the vicinity of the rim.

10. The device in accordance with claim 4, wherein the at least one piercer comprises:

at least one first piercer extendible from the first passageway into said holder and defining the second passageway; and at least one second piercer extendible into the holder at an end opposite the first piercer, said second piercer being hollow to define a passageway which is open to the interior and exterior of the holder said second piercer passageway being capable of communication with the second passageway.

11. The device in accordance with claim 10, which further comprises an engaging means for causing the first and second piercers to extend into the holder.

12. The device in accordance with claim 10 further comprising engaging means for extending the at least one second piercer into said holder.

13. The device in accordance with claim 12 further comprising a cover having at least one opening, said cover position to at least partially cover the holder.

14. A device for the oral or nasal inhalation of a finely divided material comprising:

a body member having a first and second end with a first passageway extending therethrough, said first passageway having an opening at the first end of the body member for insertion into a mouth or nose of a user and an opening at the second end of the body member for intake of air responsive to a user's inhalation;

at least one container of finely divided material associated with the body member, said container having a first and second sealed end, each end of said container being unsealable to allow expulsion of the finely divided material therefrom;

at least one piercer for piercing at least one end of the at least one container, said piercer defining a second passageway therethrough which communicates with the first passageway at a first end and an exterior of the body member at a second end, wherein when the sealed ends of the container are unsealed, air drawn through the first passageway cooperates with air drawn through the container and second passageway to dispense the finely divided material from the container.

15. The device in accordance with claim 14, wherein the container defines a height extending between the first and second ends and the at least one piercer extends from the first passageway and through the holder for a distance greater than the height of the container to both pierce and unseal the container.

16. The device in accordance with claim 14, wherein the container is a cylindrically shaped cartridge partially filled with a finely divided material.

17. The device in accordance with claim 14, wherein both the container and the at least one piercer are cylindrical and the first end of the container is disposed adjacent the body member while the container is in the holder, said container having a diameter which is about 0.005 to 0.015 inches greater than a diameter of the piercer.

18. The device in accordance with claim 14, wherein said at least one container is a disk comprising a plurality of containers each containing a finely divided material.

19. The device in accordance with claim 18, further comprising locking means for locking the disk into position each time a container is disposed adjacent the at least one piercer.

20. The device in accordance with claim 14, wherein the piercer at a piercing end is angled to about a 30° to 45° angle, an apex of said piercing end is sharpened and a rim at said piercing end opposite the apex is blunted so that a tab is created in a surface at one end of the sealed container when the piercer pierces the sealed container, said tab being hinged and held against an internal surface of the container by the piercer to avoid a user's ingestion.

* * * * *

UNITED STATES PATENT AND TRADEMARK OFFICE
CERTIFICATE OF CORRECTION

PATENT NO. : 5,715,810

DATED : February 10, 1998

INVENTOR(S) : John C. Armstrong and Richard C. J. Palson

It is certified that error appears in the above-identified patent and that said Letters Patent is hereby corrected as shown below:

Cover sheet, item [63]: Delete "which is a continuation of Ser. No. 735,924, Jul. 25, 1991, Pat. No. 5,152,722,".

Column 12, line 24: Change "seconds" to --second ends--.

Column 12, line 26: Insert --,-- after "holder".

Column 14, line 6: Change "position" to --positioned--.

Signed and Sealed this

Eleventh Day of April, 2000

Attest:

Attesting Officer

Q. TODD DICKINSON

Director of Patents and Trademarks